(12) United States Patent
Hinrichs et al.

(10) Patent No.: US 11,351,097 B2
(45) Date of Patent: Jun. 7, 2022

(54) ORAL CARE PRODUCT AND METHODS OF USE AND MANUFACTURE THEREOF

(71) Applicant: Colgate-Palmolive Company, New York, NY (US)

(72) Inventors: Ruth Hinrichs, Therwil (CH); Hans Stettler, Basel (CH); Turan Matur, Binningen (CH)

(73) Assignee: Colgate-Palmolive Company, New York, NY (US)

(*) Notice: Subject to any disclaimer, the term of this patent is extended or adjusted under 35 U.S.C. 154(b) by 447 days.

(21) Appl. No.: 16/067,045

(22) PCT Filed: Dec. 30, 2015

(86) PCT No.: PCT/US2015/068160
§ 371 (c)(1),
(2) Date: Jun. 28, 2018

(87) PCT Pub. No.: WO2017/116445
PCT Pub. Date: Jul. 6, 2017

(65) Prior Publication Data
US 2020/0268624 A1 Aug. 27, 2020

(51) Int. Cl.
*A61Q 11/00* (2006.01)
*A61K 8/34* (2006.01)
*A61K 8/21* (2006.01)
*A61K 8/365* (2006.01)
*A61K 8/81* (2006.01)

(52) U.S. Cl.
CPC .............. *A61K 8/21* (2013.01); *A61K 8/345* (2013.01); *A61K 8/365* (2013.01); *A61K 8/8176* (2013.01); *A61Q 11/00* (2013.01)

(58) Field of Classification Search
CPC .. A61Q 11/00; A61Q 17/005; A61K 2300/00; A61K 8/21; A61K 8/34; A61K 47/10; A61K 2800/92
See application file for complete search history.

(56) References Cited

U.S. PATENT DOCUMENTS

| | | | |
|---|---|---|---|
| 4,476,107 A * | 10/1984 | Schmolka ............. | A61K 8/90 424/49 |
| 4,828,822 A | 5/1989 | Muhlemann et al. | |
| 5,538,714 A * | 7/1996 | Pink ..................... | A61K 8/25 424/49 |
| 9,326,924 B1 * | 5/2016 | Fourre .................. | A61K 8/922 |
| 9,855,200 B2 | 1/2018 | Campbell et al. | |
| 9,937,115 B2 | 4/2018 | Haught et al. | |
| 2008/0213440 A1 * | 9/2008 | Harvey ................. | A23L 27/204 426/289 |
| 2009/0220625 A1 * | 9/2009 | Herrmann ............ | A61K 31/045 424/756 |
| 2010/0119461 A1 | 5/2010 | Bicard-Benhamou et al. | |
| 2011/0028566 A1 | 2/2011 | McCaulley et al. | |
| 2013/0208375 A1 | 8/2013 | Argilagos et al. | |
| 2013/0267570 A1 | 10/2013 | Premachandran et al. | |

FOREIGN PATENT DOCUMENTS

| | | | |
|---|---|---|---|
| DE | 102010000746 A1 | 1/2011 | |
| EP | 2774481 | 9/2014 | |
| JP | 2001-348308 | 12/2001 | |
| JP | 2006-104144 | 4/2006 | |
| WO | WO-9427566 A1 * | 12/1994 | .............. A61K 8/37 |
| WO | 1995/009602 | 4/1995 | |
| WO | 2001/034109 | 5/2001 | |
| WO | WO-2006087569 A2 * | 8/2006 | ............. A01N 65/24 |
| WO | 2015/158635 | 10/2015 | |

OTHER PUBLICATIONS

LyondellBasell. MPDIOL Glycol. 2011. <https://www.lyondellbasell.com/globalassets/documents/chemicals-technical-literature/lyondellbasell-chemicals-technicalliterature-mpdiol-glycol—a-product-for-the-personal-care-industry-2128.pdf> (Year: 2011).*
Varvaresou, A et al. "Review Article: Self-preserving cosmetics". International Journal of Cosmetic Science, 2009, vol. 31, pp. 163-175.
Gupta et al., 1979, "Study of the antimicrobial and preservative activities of 2-phenylethanol and its esters," Chemical Abstracts Service STN Database AN: 1979:5872285 Abstract.
International Search Report and Written Opinion of the International Searching Authority in International Application No. PCT/US2015/068157, dated Mar. 11, 2016.
Thiemann et al. 2014, "The formulator's guide to safe cosmetic preservation", Nov. 2014 Personal Care 39 https://www.dr-straetmans.de/dl/media/filer_public/7a/ef/7aef7f01-c566-425c-9c7b-500334a96b2a/review_article_about_the_development_and_trends_in_preservative_legislation_and_safe_alternatives_for_the_future_verstatil_dermosoft.pdf.
Woodruff, 2014, "Cosmetic preservation," https://creative-developments.co.uk/wp-content/uploads/2013/10/Cosmetic-Preservation-2014.pdf.
International Search Report and Written Opinion of the International Searching Authority in International Application No. PCT/US2015/068160, dated Mar. 24, 2016.
Exerkate et al., 2010, "Different Response to Amine Fluoride by *Streptococcus mutans* and Polymicrobial Biofilms in a Novel High-Throughput Active Attachment Model," Caries Research 44:372-379.
Drstraetmans, 2013, Product Brochure "Dermosoft® OMP" Product information Brochure.

* cited by examiner

Primary Examiner — Tracy Liu

(57) ABSTRACT

This invention relates to a oral care compositions, and in particular to oral care mouthrinse compositions comprising (i) at least one source of ionic tin; and (ii) an antibacterial system comprising caprylyl glycol and 3-phenyl-1-propanol, as well as to methods of using and of making these compositions.

19 Claims, No Drawings

ORAL CARE PRODUCT AND METHODS OF USE AND MANUFACTURE THEREOF

BACKGROUND

Gingival inflammation is an early stage of gum disease that affects millions of people. If not treated, gingival inflammation can lead to periodontal disease, and tooth loss. Since bacteria are the main cause of gingival inflammation, antibacterial efficacy is recognized as a prerequisite for chemical treatment of irritated gums and protection against gingival inflammation.

Accordingly, there exists a need for improved antibacterial compositions effective against bacteria that cause gingival inflammation.

BRIEF SUMMARY

It has surprisingly been found that a combination of caprylyl glycol and 3-phenyl-1-propanol can provide excellent antibacterial efficacy in oral care mouthrinse compositions containing tin ions. The compositions of the present disclosure are galenically stable and show considerably improved antibacterial efficacy. Thus, in some embodiments, the present disclosure provides oral care mouth rinse (i.e., mouthwash) compositions comprising at least one source of ionic tin; caprylyl glycol; and 3-phenyl-1-propanol. In some embodiments, the caprylyl glycol is present in an amount of from 0.01% to 1%; for example 0.1% to 0.5%; for example 0.2% to 0.3% by weight of the composition; and the 3-phenyl-1-propanol is present in an amount of from 0.01% to 0.25%; for example 0.02% to 0.1%; for example 0.03% to 0.07% by weight of the composition.

In some embodiments, the source of ionic tin is a stannous ion source, or a stannic ion source, such as stannous fluoride, stannous chloride, stannic fluoride, stannic chloride, stannic acetate and stannous acetate or a combination thereof. Preferably, the source of ionic tin is a stannous ion source, for example stannous fluoride, stannous chloride, or stannous acetate, and more preferably stannous fluoride.

In some embodiments, the compositions further comprise a fluoride ion source which is not a tin salt, for example an organic fluoride such as amine fluoride (i.e. N,N,N'-tris(2-hydroxyethyl)-N'-octadecyl-1,3-diaminopropane dihydrofluoride). In some further embodiments, the compositions further comprise polyvinylpyrrolidone, and in some further embodiments, the compositions further comprise at least one $C_3$ to $C_7$ α-hydroxy acid; or $C_4$ to $C_6$ α-hydroxy acid, which is preferably selected from malic acid, tartaric acid, α-hydroxy glutaric acid, gluconic acid, or a salt thereof, with malic acid being preferred.

In further embodiments, the oral care mouth rinse compositions of the present disclosure further comprise at least one surfactant, for example a PEG hydrogenated castor oil, such as a PEG 40 hydrogenated castor oil. In further embodiments, the oral care mouth rinse compositions can further comprise one or more humectants, sweeteners, flavorings, sensates, fragrances, dyes and/or odor neutralizing agents.

The invention further provides methods for using and making the compositions.

The invention further encompasses methods comprising applying an effective amount of an oral care mouth rinse composition of the invention to the oral cavity, e.g., rinsing the oral cavity, optionally in conjunction with brushing, to a subject in need thereof, to (i) reduce or inhibit formation of dental caries, (ii) reduce, repair or inhibit pre-carious lesions of the enamel, (iii) reduce or inhibit demineralization and promote remineralization of the teeth, (iv) reduce hypersensitivity of the teeth, (v) reduce or inhibit gingivitis, (vi) promote healing of sores or cuts in the oral cavity, (vii) reduce levels of acid producing bacteria, (viii) reduce or inhibit microbial biofilm formation in the oral cavity, (ix) reduce or inhibit plaque formation in the oral cavity, (x) promote systemic health, and/or (xi) clean teeth and oral cavity.

DETAILED DESCRIPTION

As used herein, an amount of a substance expressed as "%, by weight of the composition" is intended to mean the percentage by weight of that substance based on the total weight of the composition.

The present disclosure thus provides, in a first embodiment, oral care mouth rinse composition (Composition 1.0), comprising:
at least one source of ionic tin;
caprylyl glycol; and
3-phenyl-1-propanol, optionally in the presence of a dissolution agent, for example methylpropanediol; for example, any of the following compositions:

1.1. Composition 1.0, wherein:
the caprylyl glycol is present in an amount of from 0.01% to 1% by weight of the composition; and
the 3-phenyl-1-propanol is present in an amount of from 0.01% to 0.25% by weight of the composition.

1.2. Composition 1.0 or 1.1, wherein:
the caprylyl glycol is present in an amount of from 0.1% to 0.6% by weight of the composition; and
the 3-phenyl-1-propanol is present in an amount of from 0.02% to 0.15% by weight of the composition.

1.3. Composition 1.0 or 1.1, wherein:
the caprylyl glycol is present in an amount of from 0.2% to 0.4% by weight of the composition; and
the 3-phenyl-1-propanol is present in an amount of from 0.03% to 0.07% by weight of the composition.

1.4. Any of the foregoing compositions wherein the composition comprises at least one stannous ion source, at least one stannic ion source, or a combination thereof.

1.5. Any of the foregoing compositions wherein the composition comprises at least one stannous ion source.

1.6. Any of the foregoing compositions wherein the at least one ionic tin source is selected from stannous fluoride, stannous chloride, stannic fluoride, stannic chloride, stannic acetate and stannous acetate.

1.7. Any of the foregoing compositions wherein the at least one ionic tin source comprises stannous fluoride.

1.8. Any of the foregoing compositions wherein the tin ions are present in an amount of from 0.01% to 0.10% by weight of the oral care mouth rinse composition.

1.9. Any of the foregoing compositions wherein the tin ions are present in an amount of from 0.02% to 0.08% by weight of the oral care mouth rinse composition.

1.10. Any of the foregoing compositions wherein the tin ions are present in an amount of from 0.03% to 0.06% by weight of the oral care mouth rinse composition.

1.11. Any of the foregoing compositions wherein the tin ions are present in an amount of from 0.035% to 0.045% by weight of the oral care mouth rinse composition.

1.12. Any of the foregoing compositions further comprising a fluoride ion source which is not a tin salt.

1.13. Any of the foregoing compositions further comprising an organic fluoride, e.g., amine fluoride (i.e., N,N,N'-tris(2-hydroxyethyl)-N'-octadecyl-1,3-diaminopropane dihydrofluoride).

1.14. Composition 1.13, wherein the amine fluoride is present in an amount of from 0.01 to 0.4% by weight; or from 0.1% to 0.3% by weight; or about 0.17% by weight, of the composition.

1.15. Any of the foregoing compositions, wherein the composition comprises an organic fluoride and stannous fluoride in an amount such that they together provide from about 0.01-0.04%; for example from about 0.02-0.05%; for example about 0.026% fluoride ions by weight in the mouth rinse composition.

1.16. Composition 1.15, wherein the organic fluoride is amine fluoride.

1.17. Composition 1.16, wherein the stannous fluoride and the amine fluoride each provide fluoride ions in an amount of about 0.013% by weight of the composition.

1.18. Any of the foregoing compositions further comprising polyvinylpyrrolidone in an amount of from 0.1% to 4% by weight based on the total weight of the oral care mouth rinse composition.

1.19. Any of the foregoing compositions further comprising polyvinylpyrrolidone in an amount of from 0.15% to 2.5%, by weight of the composition.

1.20. Any of the foregoing compositions further comprising at least one $C_3$ to $C_7$ α-hydroxy acid; or a $C_4$ to $C_6$ α-hydroxy acid.

1.21. Composition 1.20, wherein the at least one α-hydroxy acid is selected from malic acid, tartaric acid, α-hydroxy glutaric acid, gluconic acid, and salts thereof.

1.22. Composition 1.20 or 1.21, wherein the at least one α-hydroxy acid or salt thereof is selected from malic acid and sodium-D-gluconate.

1.23. Composition 1.20, wherein the at least one α-hydroxy acid is malic acid, in an amount of from 0.01% to 0.8% by weight; or from 0.05% to 0.5% by weight; or from 0.08% to 0.3% by weight; or from 0.1% to 0.2% by weight of the composition.

1.24. Any of the foregoing compositions further comprising at least one surfactant.

1.25. Composition 1.24, wherein the at least one surfactant comprises a PEG hydrogenated castor oil, in an amount of, for a 90% PEG hydrogenated castor oil composition, from 0.01% to 3%; or 0.05% to 1%; or 0.1% to 0.5%; or from 0.2% to 0.4% by weight of the composition.

1.26. Any of the foregoing compositions further comprising one or more humectants, sweeteners, flavorings, sensates, fragrances, colorants, dyes and/or odor neutralizing agents.

1.27. Any of the foregoing compositions wherein the dissolution agent is selected from methylpropanediol, a surfactant, an amine, amine base, an organic fluoride, amine fluoride, propylene glycol, or cocamidopropyl betaine; or mixtures of two or more thereof 1.28. Any of the foregoing compositions effective upon application to the oral cavity, e.g., by rinsing, optionally in conjunction with brushing, to (i) reduce or inhibit gingivitis, (ii) promote healing of sores or cuts in the mouth, (iii) inhibit microbial biofilm formation in the oral cavity, (iv) treat, relieve or reduce dry mouth, (v) clean the teeth and oral cavity and/or (vi) promote systemic health, including cardiovascular health, e.g., by reducing potential for systemic infection via the oral tissues.

1.29. A composition obtained or obtainable by combining the ingredients as set forth in any of the preceding compositions.

In another embodiment, the present disclosure provides a method (Method 1) to:
  (i) reduce or inhibit formation of dental caries,
  (ii) reduce, repair or inhibit pre-carious lesions of the enamel,
  (iii) reduce or inhibit demineralization and promote remineralization of the teeth,
  (iv) reduce hypersensitivity of the teeth,
  (v) reduce or inhibit gingivitis,
  (vi) promote healing of sores or cuts in the oral cavity,
  (vii) reduce levels of acid producing bacteria,
  (viii) reduce or inhibit microbial biofilm formation in the oral cavity,
  (ix) reduce or inhibit plaque formation in the oral cavity,
  (x) promote systemic health, or
  (xi) clean teeth and oral cavity,
  comprising applying an effective amount of an oral care mouth rinse composition according to any preceding compositions to the oral cavity of a subject in need thereof.

In another embodiment, the invention encompasses a method (Method 2) to improve oral health comprising applying an effective amount of the oral composition of any of the embodiments set forth above to the oral cavity of a subject in need thereof.

In a further embodiment, the disclosure provides a method (Method 3) for preparing an oral care mouthrinse comprising: combining together (i) at least one source of ionic tin; (ii) caprylyl glycol; and (iii) 3-phenyl-1-propanol; in an aqueous solution, together with a source of fluoride ions, wherein the source of fluoride ions is separate from the source of ionic tin.

In a further embodiment, the invention provides the use of any of the foregoing oral care mouth rinse compositions to:
  (i) reduce or inhibit formation of dental caries,
  (ii) reduce, repair or inhibit pre-carious lesions of the enamel,
  (iii) reduce or inhibit demineralization and promote remineralization of the teeth,
  (iv) reduce hypersensitivity of the teeth,
  (v) reduce or inhibit gingivitis,
  (vi) promote healing of sores or cuts in the oral cavity,
  (vii) reduce levels of acid producing bacteria,
  (viii) reduce or inhibit microbial biofilm formation in the oral cavity,
  (ix) reduce or inhibit plaque formation in the oral cavity,
  (x) promote systemic health, or
  (xi) clean teeth and oral cavity;
  in a subject in need thereof.

The present disclosure further provides the use of the combination of a source of ionic tin, caprylyl glycol and 3-phenyl-1-propanol, and optionally a dissolution agent such as, for example and not limitation, methylpropanediol, in the manufacture of a composition of the invention, e.g., for use in any of the indications set forth in the above method.

The present disclosure further provides a method to increase the antibacterial efficacy of an oral care mouth rinse composition comprising formulating the oral care composition to comprise caprylyl glycol and 3-phenyl-1-propanol.

In some embodiments, the compositions of the invention are intended to be used as a mouth rinse, delivering a dose of the ionic tin, fluoride and antibacterial system comprising caprylyl glycol and 3-phenyl-1-propanol, optionally in the presence of a dissolution agent, for example methylpropanediol, as well as other added actives, to the oral cavity of a subject.

The present compositions are intended for topical use in the mouth and so salts for use in the present invention should be safe for such use, in the amounts and concentrations provided. Suitable salts include salts known in the art to be pharmaceutically acceptable salts are generally considered to be physiologically acceptable in the amounts and concentrations provided. Physiologically acceptable salts include those derived from pharmaceutically acceptable inorganic or organic acids or bases, for example acid addition salts formed by acids which form a physiological acceptable anion, e.g., hydrochloride or bromide salt, and base addition salts formed by bases which form a physiologically acceptable cation, for example those derived from alkali metals such as potassium and sodium or alkaline earth metals such as calcium and magnesium. Physiologically acceptable salts may be obtained using standard procedures known in the art, for example, by reacting a sufficiently basic compound such as an amine with a suitable acid affording a physiologically acceptable anion.

Source of Ionic Tin

The mouth rinse compositions of the present disclosure comprise a source of ionic tin. In certain embodiments the source of ionic tin is a source of stannous (Sn(II)) or stannic (Sn(IV)) ions. In certain embodiments the source of ionic tin comprises at least one stannous ion source, at least one stannic ion source or a combination thereof. In certain embodiments the source of ionic tin comprises at least one stannous ion source. In certain embodiments the source of ionic tin comprises a stannous salt. In certain embodiments the source of ionic tin is selected from water-soluble tin salts such as stannous fluoride, stannous chloride, stannic fluoride, stannic chloride, stannic acetate, stannous acetate and combinations thereof. In certain embodiments the source of ionic tin is selected from stannous fluoride, stannous chloride, stannous acetate and combinations thereof. In certain embodiments the source of ionic tin comprises stannous fluoride, stannous chloride and/or combinations thereof. In certain preferred embodiments, the source of ionic tin is a stannous ion source. In particularly preferred embodiments the source of ionic tin is stannous fluoride. In certain embodiments separate soluble stannous and fluoride salts may be used to provide stannous fluoride in situ. Alternatively, stannous fluoride salt may be added to the composition directly.

In certain embodiments the ionic tin is present in the oral care mouth rinse composition in an amount (assuming complete dissolution of the tin salt) sufficient to provide tin ions, preferably stannous ions, in an amount of from 0.01% to 0.10% by weight of the oral care mouth rinse composition; or in an amount of from 0.02% to 0.08% by weight of the oral care mouth rinse composition; or in an amount of from 0.03% to 0.06% by weight of the oral care mouth rinse composition; or in an amount of from 0.035% to 0.045% by weight of the oral care mouth rinse composition.

Antibacterial System

The compositions disclosed herein include an antibacterial system that comprises caprylyl glycol (octane-1,2-diol; CAS Registry Number 1117-86-8) and 3-phenyl-1-propanol (3-phenylpropan-1-ol; CAS Registry Number 122-97-4). In some embodiments, the caprylyl glycol is present in an amount of from 0.01% to 1%; for example 0.1% to 0.5%; for example 0.2% to 0.3% by weight of the composition; and the 3-phenyl-1-propanol is present in an amount of from 0.01% to 0.25%; for example 0.02% to 0.1%; for example 0.03% to 0.08% by weight of the composition.

It has been discovered that this combination provides superior antibacterial properties in oral care mouthrinse compositions, and in particular, those in accordance with the present invention that contains a source of ionic tin.

In some embodiments, the caprylyl glycol and 3-phenyl-1-propanol can be present in the mouth rinse compositions in a ratio of from 8:1 to 3:1; for example from 6:1 to 4:1; for example about 5:1 by weight.

In some embodiments, caprylyl glycol and 3-phenyl-1-propanol can be prepared as a mixture that can be added to the composition during processing. The caprylyl glycol is typically present in the mixture in an amount of from 4% to 20%; for example 10% to 20%; for example 13% to 18%; for example 14%-16% by weight of the mixture; and the 3-phenyl-1-propanol is typically present in the mixture in an amount of from 0.5% to 10%; for example 1% to 5%; for example 2% to 4%, for example 2.5% to 4% by weight of the mixture. In some embodiments, the mixture can contain one or more dissolving agents (also known as a dissolution agents). Examples of suitable dissolution agents include, without limitation, methylpropanediol (2-methylpropane-1,3-diol; CAS Registry Number 2163-42-0), a surfactant, an amine, amine base, an organic fluoride, amine fluoride, propylene glycol, or cocamidopropyl betaine; or mixtures of two or more thereof. The dissolving agent or agents can be present in the mixture in a combined amount of from 50% to 95%; for example 75% to 95%; for example 75% to 85%; for example 80% to 83% by weight of the mixture.

It will be appreciated that in some embodiments, the addition of a separate dissolution agent is not required due to the dissolving capacity of other ingredients. For example, a composition according to the present disclosure containing one or more of sufficient amine base, amine fluoride, surfactant, other ingredient or combination thereof that is effective to dissolve the caprylyl glycol and 3-phenyl-1-propanol does not require a further dissolution agent.

In some embodiments, the dissolution agent is the organic portion of an organic fluoride as described below, which are typically amines. One preferred organic dissolution agent is known as "amine base", which is intended to denote herein the base portion of amine fluoride—i.e., the compound N,N,N'-tris(2-hydroxyethyl)-N'-octadecyl-1,3-diaminopropane. In some embodiments, the present compositions contain an amount of amine base in addition to the amine fluoride. In some embodiments, the compositions include amine base in an amount of from 0.01% to 2%; or from 0.01 to 1%, or from 0.01 to 0.10%, by weight of the composition.

The amount of mixture can be conveniently selected to provide the amounts of caprylyl glycol and 3-phenyl-1-propanol in the final composition as described above. Thus, the mixture comprising the caprylyl glycol and 3-phenyl-1-propanol and, optionally, the dissolution agent, can be included in the present compositions in an amount of from 0.5% to 10%; for example 1% to 6%; for example from 1% to 5%; for example from 1% to 3%, for example from 1% to 2%, for example from 1.4% to 1.8%, by weight; for example from 1.5% to 1.7% by weight of the composition. In some preferred embodiments, the dissolution agent is methylpropanediol. A suitable mixture containing caprylyl glycol, 3-phenyl-1-propanol and methylpropanediol is marketed by Dr. Straetmans Chemische Produkte GmbH, Hamburg, Germany, under the name Dermosoft OMP.

Fluoride Ion Source

The oral care compositions can further include one or more fluoride ion sources, e.g., soluble fluoride salt that is not a tin salt—i.e., that is separate from fluoride ions provided by the stannous or stannic salt. A wide variety of fluoride ion-yielding materials can be employed as sources of soluble fluoride in the present compositions. Examples of suitable fluoride ion-yielding materials are found in U.S. Pat. No. 3,535,421, to Briner et al.; U.S. Pat. No. 4,885,155, to Parran, Jr. et al. and U.S. Pat. No. 3,678,154, to Widder et al., incorporated herein by reference.

Representative non-tin fluoride ion sources include, but are not limited to, sodium fluoride, potassium fluoride, sodium monofluorophosphate, sodium fluorosilicate, ammonium fluorosilicate, amine fluoride, ammonium fluoride, and combinations thereof. Where the formulation comprises calcium salts, the fluoride salts are preferably salts wherein the fluoride is covalently bound to another atom, e.g., as in sodium monofluorophosphate, rather than merely ionically bound, e.g., as in sodium fluoride. In certain embodiments the non-tin fluoride ion source includes or consists of an organic fluoride, also known as organic amine fluorides. Representative examples of organic fluorides can be found in, for example, European Patent No. EP19970911101, incorporated by reference herein in its entirety. One preferred organic fluoride is referred to herein as "amine fluoride", (or "AmF"), and is the compound N,N,N'-tris(2-hydroxyethyl)-N'-octadecyl-1,3-diaminopropane dihydrofluoride (also known as "Olaflur", and sometimes written as N,N,N'-tris(2-hydroxyethyl)-N'-octadecyl propane-1,3-diamine dihydrofluoride). While the term "amine fluoride" as used herein denotes the compound N,N,N'-tris(2-hydroxyethyl)-N'-octadecyl-1,3-diaminopropane dihydrofluoride, it will be appreciated that any of the variety of organic fluorides that are known to be useful in mouth rise compositions can be employed instead of, or in addition to, amine fluoride. In certain embodiments, amine fluoride is present in an amount of from 0.05% to 1.5% by weight; or from 0.08% to 1.0% by weight, or about 0.17% by weight of the composition. In some embodiments, the amount of the organic fluoride, (e.g., amine fluoride) and stannous fluoride are selected such that they together provide from about 0.01-0.04%; for example from about 0.02-0.05%; for example about 0.026% fluoride ions by weight in the mouth rinse composition. In certain embodiments, the compositions of the disclosure comprise stannous fluoride and amine fluoride, in amounts that provide approximately equal amounts of fluoride ion; for example about 0.013% each by weight of the composition.

Polyvinylpyrrolidone

In some embodiments, the compositions of the present disclosure contain polyvinylpyrrolidone (PVP), also known as polyvidone or povidone. PVP is a water-soluble polymer made from the monomer N-vinylpyrrolidone which has been shown reduce tooth staining by various compounds including ionic tin, without compromising oral care efficacy. Polyvinylpyrrolidone can have a molar mass of from 2,500 to 3,000,000 Daltons.

In certain embodiments the PVP in the compositions of the present disclosure has a molar mass of from 10,000 to 300,000 Daltons, for example 20,000 to 100,000 or 40,000 to 75,000 Daltons. In certain embodiments the PVP has a molar mass of about 58,000 Daltons. One such PVP polymer especially suitable for use in the compositions of the invention is sold by Ashland, Inc., Covington, Ky. under the name Plasdone K-29/32.

Typically, the PVP is present in the oral care mouth rinse formulations of the present disclosure in an amount from 0.1% to 4%, or 0.15% to 3% by weight of the composition.

α-Hydroxy Acid

In some embodiments, the compositions of the present disclosure include at least one α-hydroxy acid or salt thereof. In some embodiments, the salt of the at least one α-hydroxy acid is the sodium salt or the potassium salt. In some embodiments, the salt is the sodium salt. In some embodiments, the at least one α-hydroxy acid is a $C_3$ to $C_7$ α-hydroxy acid, or a $C_4$ to $C_6$ α-hydroxy acid. In certain embodiments, the at least one α-hydroxy acid is malic acid, tartaric acid, α-hydroxy glutaric acid, gluconic acid, or a salt thereof. In certain embodiments, the at least one α-hydroxy acid or salt thereof is selected from malic acid and sodium-D-gluconate.

In some embodiments, the at least one α-hydroxy acid or salt thereof is malic acid. In certain embodiments, the malic acid is a racemic mixture of L-malic acid and D-malic acid. In some embodiments, the malic acid is present in an amount of from 0.01% to 0.5%; for example from 0.05% to 0.3%; for example from 0.1% to 0.2%, by weight of the composition.

Surfactant

In some embodiments, the compositions of the present disclosure include at least one surfactant or solubilizer. Suitable surfactants include neutral surfactants (such as polyoxyethylene hydrogenated castor oil or fatty acids of sugars), anionic surfactants (such as sodium lauryl sulfate), cationic surfactants (such as the ammonium cation surfactants) or zwitterionic surfactants. These surfactants or solubilizers can be present in amounts of typically 0% to 2%, preferably 0.2% to 1% by weight of the oral care composition. In some preferred embodiments, the compositions of the present disclosure include at least one surfactant that is a polyoxyethylene (polyethylene glycol; PEG) hydrogenated castor oil. In some such embodiments, the compositions of the present disclosure include a PEG-40 hydrogenated castor oil, in an amount of, for a 90% composition of PEG hydrogenated castor oil, from 0.01% to 2%; or 0.05% to 1%; or 0.1% to 0.5%; or about 0.25% by weight of the composition. Suitable PEG-40 hydrogenated castor oils include, for example, those sold by BASF under the name Cremophor RH 410 and Cremophor RH 40. Those of skill in the art will appreciate that for PEG-40 hydrogenated castor oils having higher percentages of active, for example Cremophor RH 40, which is typically provided as a pure (i.e., 100%) composition of PEG hydrogenated castor oil, a correspondingly smaller amount of such PEG-40 hydrogenated castor oil would be employed.

Polyhydric Alcohol

In any of the above embodiments, the compositions can further comprise one or more polyhydric alcohols such as xylitol, glycerine, sorbitol, propylene glycol and combinations thereof. In certain embodiments the compositions can optionally comprise from about 0.10% to about 10% polyhydric alcohol by weight of the composition. In certain embodiments the compositions can comprise xylitol in an amount of from 0.50% to 10%, for example from 0.50% to 7.0%, for example from 1% to 5%, for example 2.5% xylitol, by weight of the composition.

Sweeteners

In any of the above embodiments, the compositions can further comprise a sweetener such as, for example, saccharin, for example sodium saccharin, acesulfam, neotame, cyclamate or sucralose; natural high-intensity sweeteners such as thaumatin, stevioside or glycyrrhizin; or such as sorbitol, xylitol, maltitol or mannitol. One or more such sweeteners can be present in an amount of from 0.005% to 5% by weight, for example 0.01% to 1%, for example 0.01% to 0.1%, for example 0.06% by weight of the composition.

Colorants

One or more colorants can be included in the compositions of the present disclosure. Colorants can include pigments, dyes, lakes and agents imparting a particular color or visual quality to the composition. Any orally acceptable colorant can be used. One or more colorants can optionally be present in the compositions in an amount of from 0.00001% to 2%, for example from 0.0001% to 1%, for example from 0.00015% to 0.7% of the composition by weight.

Humectants

Humectants can reduce evaporation and also contribute towards preservation by lowering water activity, and can also impart desirable sweetness or flavor to compositions. Suitable humectants include edible polyhydric alcohols such as glycerin, sorbitol, xylitol, propylene glycol as well as other polyols and mixtures of these humectants. Other useful materials can also include orally acceptable alcohols, or polymers, e.g., such as polyvinylmethyl ether maleic acid copolymers, polysaccharides (e.g. cellulose derivatives, for example carboxymethyl cellulose, or polysaccharide gums, for example xanthan gum or carrageenan gum).

Preservatives

A wide variety of preservatives can be used in the compositions of the present disclosure. Suitable preservatives include, for example, sodium benzoate, potassium sorbate, methylisothiazolinone, paraben preservatives, for example methyl p-hydroxybenzoate, propyl p-hydroxybenzoate, and mixtures thereof.

Flavoring Agents

The oral care compositions of the present disclosure can also include a flavoring agent. Flavoring agents include, but are not limited to, essential oils and various flavoring aldehydes, esters, alcohols, and similar materials, as well as sweeteners such as sodium saccharin. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. The flavoring agent is typically incorporated in the oral composition at a concentration of 0.01 to 1.5% by weight.

Anti-Calculus Agents

In some embodiments, the oral compositions of the present disclosure include antitartar agents to prevent and/or minimize calculus formation. One or more of such agents can be present. Suitable anticalculus agents include without limitation: stannous, copper, magnesium and strontium salts, dimethicone copolyols such as cetyl dimethicone copolyol, glucoamylase, glucose oxidase, urea, calcium lactate, calcium glycerophosphate, strontium polyacrylates and chelating agents such as citric and tartaric acids and alkali metal salts thereof, and salts of EDTA, for example tetrasodium EDTA; and phosphates and polyphosphates. Phosphate and polyphosphate salts are generally employed in the form of their wholly or partially neutralized water soluble cationic species (e.g., potassium, sodium or ammonium salts, and any mixtures thereof). Thus, useful inorganic phosphate and polyphosphate salts illustratively include monovalent cations with monobasic, dibasic and tribasic phosphates; tripolyphosphate and tetrapolyphosphate; mono-, di-, tri- and tetra-pyrophosphates; and cyclophosphates (also generally known in the art as "metaphosphates"). Useful monovalent cations of such phosphate salts include hydrogen, monovalent metals including alkali metals, and ammonium, for example.

Sensates

In some embodiments, the oral compositions of the present invention comprise one or more sensates—i.e., ingredients which impart some kind of sensation to the oral cavity. Suitable sensates include without limitation, physiological cooling agents including 1-menthol and 3-(1-menthoxy) propane-1,2-diol, peppermint oil, N-substituted-p-menthane-3-carboxamides, acyclic tertiary and secondary carboxamides, and 3-1-menthoxy propan-1,2-diol (see, e.g., PCT Published Application Number WO 97/06695); heating and/or warming sensates such as, for example and not imitated to, vanillyl alcohol n-butyl ether (vanillyl butyl ether), vanillyl alcohol n-propyl ether, vanillyl alcohol isopropyl ether, vanillyl alcohol isobutyl ether, vanillyl alcohol n-amino ether, vanillyl alcohol isoamyl ether, vanillyl alcohol n-hexyl ether, vanillyl alcohol methyl ether, vanillyl alcohol ethyl ether, gingerol, shogaol, paradol, zingerone, capsaicin, dihydrocapsaicin, nordihydrocapsaicin, homocapsaicin, homodihydrocapsaicin, ethanol, iso-propyl alcohol, isoamyl alcohol, benzyl alcohol, chloroform, eugenol, cinnamon oil, connamic aldehyde and phosphate derivatives of same; materials that are known to cause a tingling, numbing and/or stinging sensation and are used in foods as popular spice and/or herb condiments; and combinations thereof.

Odor Neutralizing Agents

In some embodiments, the oral compositions of the present disclosure comprise one or more odor-neutralizing agents. Suitable odor neutralizing agents include, without limitation, chlorine dioxide; peroxides such a hydrogen peroxide; chlorite salts and bicarbonate salts, —e.g. sodium chlorite and sodium bicarbonate; essential oils such as eucalyptol, menthol, methyl salicylate and thymol; flavor cocktails; and zinc salts such as, for example and not limited to, zinc chloride, zinc citrate, zinc acetate, zinc sulfate, and zinc phenolsulfate.

The compositions of the present disclosure can comprise a saliva stimulating agent useful, for example, in amelioration of dry mouth. One or more saliva stimulating agents are optionally present in saliva stimulating effective total amount.

The compositions of the present disclosure can include antisensitivity agents. Such agents can be added in effective amounts, e.g., from about 0.1 wt. % to about 5 wt. % by weight based on the total weight of the composition, depending on the agent chosen.

In any of the above embodiments, the compositions can further comprise a pH adjuster. For example the compositions can comprise an acid or base in an amount sufficient to adjust the pH of the compositions such that the compositions have a pH of from 3.0 to 8.0.

Water

Water is present in the oral compositions of the invention. Water, employed in the preparation of commercial oral compositions should be deionized and free of organic impurities. Water commonly makes up the balance of the compositions and includes 10% to 99%, e.g., 40% to 98.5%, e.g., 80% to 98.5%, e.g., 85% to 98% by weight of the oral compositions. This amount of water includes the free water which is added plus that amount which is introduced with other materials or any components of the invention.

As will be evident to one of skill in the art, some components of the present compositions may perform multiple functions, and the identification of a compound as having one function herein is not meant to exclude its use for other functions in a particular composition. For example, a compound such as xylitol can function in the compositions of the invention as a sweetener, but also act as a humectant.

The present invention in its method aspect involves applying to the oral cavity a safe and effective amount of the compositions described herein. The compositions and methods according to the present disclosure are useful, inter alia, to cleanse and/or lubricate the oral cavity of a mammal, for example a human, and in particular to clean and/or lubricate the oral cavity and provide improved methods of promoting oral health and/or systemic health, including cardiovascular health, e.g., by reducing bacterial levels in the oral cavity.

Enhancing oral health also provides benefits in systemic health, as the oral tissues can be gateways for systemic infections. Good oral health is associated with systemic health, including cardiovascular health. The compositions and methods of the invention are thus useful to enhance systemic health, including cardiovascular health.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls. It is understood that when formulations are described, they may be described in terms of their ingredients, as is common in the art, notwithstanding that these ingredients may react with one another in the actual formulation as it is made, stored and used, and such products are intended to be covered by the formulations described.

EXAMPLES

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

Example 1—Representative Formulation of the Invention

Table 1 below shows a representative formulation according to the invention, and a specific embodiment (Composition 1).

TABLE 1

| Ingredient | Weight % Range |
|---|---|
| DI Water | 80-98 |
| Xylitol | 1-5 |
| PVP | 0.1-4 |
| methylpropanediol | 0.4-5 |
| caprylyl glycol | 0.07-1 |
| 3-phenyl-1-propanol | 0.01-0.25 |
| Amine Fluoride | 0.05-1.5 |
| Stannous Fluoride | 0.01-0.08 |
| PEG-40 hydrogenated castor oil (90%) | 0.05-1 |
| Malic Acid | 0.01-0.5 |
| Sweetener | 0.01-0.1 |
| Dye | 0.0001-0.1 |

TABLE 1-continued

| Ingredient | Weight % Range |
|---|---|
| Aroma | 0.05-0.2 |
| KOH (20%) | 0.1-1 |

TABLE 2

| Ingredient | Composition 1 |
|---|---|
| DI Water, sweetener, dye, aroma | 89.1652 |
| Xylitol | 2.5 |
| PVP | 2.4 |
| methylpropanediol | 3.2-3.3 |
| caprylyl glycol | 0.6-0.7 |
| 3-phenyl-1-propanol | 0.1-0.15 |
| Amine Fluoride | 0.17 |
| Stannous Fluoride | 0.054 |
| PEG-40 hydrogenated castor oil (90%) | 0.25 |
| Malic Acid | 0.17 |
| Sweetener | 0.05 |
| Dye | 0.0002 |
| Aroma | 0.115 |
| KOH (20%) | 0.44 |

A galenically stable composition (Composition 1) was prepared as described above in Table 2.

Example 2—Anti-Bacterial Efficacy of Stannous-Based Mouth Rinses

Anti-bacterial efficacy and effects on bacterial metabolism were evaluated for a composition according to the invention (Composition 1) and several stannous-based mouth rinse formulas in an active-attachment biofilm model (Exterkate et al., Caries Research 2010; 44:372.379).

Experimental Specifications

Parameters: Viable counts (Log CFU/ml), lactate production ($\mu$M)

Treatment time: 10 min

Treatment schedule: 7 times; at 24 h, 32 h, 48 h, 56 h 72 h, 80 h and 96 h

Inoculum: Native saliva

Biofilm Formation: The biofilm model consists of a metal lid with 24 clamps carrying hydroxyapatite (HAP) disks. The model was inoculated in 24-well plates with native saliva. Biofilms were formed via active recruitment of bacteria onto free-hanging HAP disks. After an initial attachment phase of 8 hours under anaerobic conditions at 37° C., the biofilms were transferred into fresh growth media for maturation. Two lids were used for this assay.

Treatment: Treatment was performed after formation of a 24 hour biofilm. To begin with, the lid was moved up and down 10 times in growth medium to remove loose cells. The lid was then transferred to a 24-well plate containing 1.6 ml of mouth rinse solution and was incubated for 10 minutes at room temperature. The lid was subsequently transferred to a new plate for washing with 1.7 ml Cysteine Peptone Water (CPW) and moved up and down 10 times to wash away the treatment solutions. This procedure was performed three times, each time with fresh CPW in a 24-well plate. The biofilms were then transferred into growth media and incubated anaerobically at 37° C. up to the next treatment exposure. There were 4 biofilm replicates for each test product (N=4).

Lactic Acid Formation: Lactic acid production was determined to assess the residual metabolic activity of biofilms after repeated exposure to test products. After the last treatment, the lid was placed on a plate containing 1.5 ml of Buffered Peptone Water+0.2% sucrose. The plate was incubated anaerobically at 37° C. for 3 hours for lactic acid formation. Subsequently, the Buffered Peptone Water solution was transferred into Eppendorf tubes and placed on a hot plate at 80° C. for 5 minutes to stop lactic acid production. After cooling to room temperature, the tubes were stored at −20° C. until analysis. Right before the assay, the tubes were centrifuged at 14,000 rpm for 10 minutes at 4° C. The assay was conducted using a L-Lactate Assay Kit according to the manufacturer's protocol (Cayman Chemical Company, Cat. No. 700510).

Assessment of Bacterial Growth: Colony forming unites (CFUs) were determined to assess the anti-bacterial efficacy of test solutions after repeated exposure to biofilms. HAP disks were removed from the lid and transferred to 1.5 ml CPW for sonication. The sonication was carried out for 2 min with 30 pulses. The volume of each suspension was brought to 2 ml. The suspension was serially diluted, plated on TSA-blood agar plates and incubated anaerobically for 48-72 h. CFUs were determined by colony counting.

Statistical Analysis: Statistical analysis was performed using Minitab 16 Software. ANOVA and Tukey test were performed on available CFU counts and lactic acid values.

Composition 1 was evaluated against a total of 9 formulations as shown in Table 3.

Composition 1 appears as Formula 4 in Table 3. Formulas 2, 3, 4, and 5 were compared against water as a negative control, and a commercial formulation containing AmF/SnF$_2$ as a positive control (Formula 1). In a separate experiment, Formulas 1 and 6-9 were evaluated against water as a negative control, and a commercial formulation containing chlorhexidine digluconate as a positive control (Formula 10).

Composition 1 (Formula 4) was clearly the most effective formula with superior antibacterial activity versus the positive control Formula 1 (AmF/SnF$_2$). All other formulas were comparable to the positive control with Formula 2 (malic acid) and Formula 5 (malic acid and SnCl$_2$) being the closest in reaching the positive control.

The anti-bacterial efficacy tests for Formulas 6-9 employed a lower detection limit and a positive control that is a commercial formulation containing chlorhexidine digluconate (Formula 10). The evaluation of the anti-bacterial efficacy again showed that Composition 1 (Formula 4) with the combination of AmF/SnF$_2$, methylpropanediol, caprylyl glycol and 3-phenyl-1-propanol was most efficacious. Caprylyl glycol and 3-phenyl-1-propanol were separately tested (Formulas 8 and 9, respectively) and also showed slight improved efficacy versus the AmF/SnF$_2$ base formulation (Formula 7) although not to the level of Composition 1. Evaluation of the metabolic activity showed that the formula containing methylpropanediol, caprylyl glycol and 3-phenyl-1-propanol in combination with AmF/SnF$_2$ was able to significantly decrease metabolic activity versus the AmF/SnF$_2$ base formula.

In a separate series of experiments, a mouth rinse containing 0.2% malic acid (Formula 11) was evaluated as described above against a series of samples of Formula 11 additionally containing caprylyl glycol and 3-phenyl-1-propanol. Water was used as negative control, and Formula 10 described above as a positive control, as shown below in Table 4:

TABLE 3

| Formula | Xylitol [%] | PVP [%] | PEG-40 hydrogenated castor oil 90% [%] | Sodium saccharin [%] | SnF$_2$ [%] | AmF [%] | SnCl$_2$ 35% [%] | Malic acid [%] | Glycerin 99.5% [%] | 3-Phenyl-1-propanol [%] | Caprylyl glycol [%] | Methyl-propanediol [%] | Chlorhexidine digluconate [%] |
|---|---|---|---|---|---|---|---|---|---|---|---|---|---|
| 1 | 5 | 2.4 | 0.35 | 0.02 | 0.0541 | 0.17 | 0 | 0 | 3 | 0 | 0 | 0 | |
| 2 | 5 | 2.4 | 0.35 | 0.02 | 0.0541 | 0.17 | 0 | 0.15 | 3 | 0 | 0 | 0 | |
| 3 | 2.5 | 2.4 | 0.35 | 0.05 | 0.0541 | 0.17 | 0 | 0.15 | 0 | 0 | 0 | 0 | |
| 4 | 2.5 | 2.4 | 0.25 | 0.05 | 0.0541 | 0.17 | 0 | 0.17 | 0 | 0 | 0.12 | 0.6 | 3.2 |
| 5 | 2.5 | 2.4 | 0.25 | 0.05 | 0.0420 | 0.207 | 0.263 | 0.2 | 0 | 0 | 0 | 0 | |
| 6 | 2.5 | 2.4 | 0.25 | 0.05 | 0 | 0.17 | 0 | 0.17 | 0 | 0 | 0 | 0 | |
| 7 | 2.5 | 2.4 | 0.25 | 0.05 | 0.0541 | 0.17 | 0 | 0.17 | 0 | 0 | 0 | 0 | |
| 8 | 2.5 | 2.4 | 0.25 | 0.05 | 0.0541 | 0.17 | 0 | 0.17 | 0 | 0 | 0.6 | 0 | |
| 9 | 2.5 | 2.4 | 0.25 | 0.05 | 0.0541 | 0.17 | 0 | 0.17 | 0 | 0.12 | 0 | 0 | |
| 10 | | | | | | | | | | | | | 0.2 |

The evaluation of anti-bacterial efficacy comparing Formulas 1-5 showed that with the exception of Formula 4 (Composition 1) all experimental mouth rinse formulas performed comparable to the positive control formula 1 (AmF/SnF2). Formula 4 (Composition 1) performed significantly better than all other formulas.

The metabolic activity of biofilms comparing Formulas 1-5 was determined after the last treatment. All test formulas were able to significantly reduce bacterial metabolism, although Formula 3 (low malic acid, low xylitol, no glycerol) was significantly less effective than the positive control which may be indicative of unfavorable interactions with actives. All other test formulas were comparable to the positive control.

TABLE 4

| Formula | Malic Acid (% w/w) | 3-Phenyl-1-propanol (% w/w) | Caprylyl glycol (% w/w) | Methylpropanediol (% w/w) |
|---|---|---|---|---|
| 11 | 0.2 | 0 | 0 | 0 |
| 12 | 0.2 | 0.13* | 0.62** | 3.25*** |
| 13 | 0.2 | 0.06 | 0.3 | 1.6 |
| 14 | 0.2 | 0.03 | 0.15 | 0.08 |
| 15 | 0.2 | 0.12 | 0.6 | 0 |
| 16 | 0.14 | 0.06 | 0.6 | 0 |
| 10 | 0 | 0 | 0 | 0 |

*approximate; values are +/−0.01%; i.e., 0.12-0.14% 3-phenyl-1-propanol
**approximate; values are +/−0.02%; i.e., 0.6-0.64% caprylyl glycol
**approximate; values are +/−0.03%; i.e., 3.22-3.28% methylpropanediol The evaluation of the anti-bacterial efficacy as described above again showed that the Formulas containing 3-phenyl-1-propanol and caprylyl glycol were very efficacious. Efficacy correlated with increasing concentration of 3-phenyl-1-propanol and caprylyl glycol, with Formula 12 showing the most effect. All formulas containing 3-phenyl-1-propanol and caprylyl glycol showed an increase of antibacterial activity over control, including Formula 14. Formulas 15 and 16, which lack dissolving agent methylpropanediol, showed efficacy comparable with Formula 12, indicating that the methylpropanediol does not contribute to the bacterial efficacy. All of the Formulas displayed results similar to positive control Formula 10 in a metabolic activity evaluation performed as described above.

The results show that the combination of and 3-phenyl-1-propanol and caprylyl glycol is very potent when combined with stannous ions. While not wishing to be bound by any particular theory, it is believed that the combination of 3-phenyl-1-propanol and caprylyl glycol may increase the bioavailability of stannous ions and therefore indirectly improves the anti-bacterial profile, or, alternatively, may increase penetration of stannous ions into bacterial cells.

Example 3—Appearances of Compositions Over Time

The appearance (color and texture) of Formula 7 (Composition 1) was determined after 3 months at 25° C. and 40° C., and was found to be comparable to a the commercial formulation Formula 1.

The formulations were evaluated using a 5 point scale from 4 (best) to 0 (fail). The results are shown below in Tables 5 and 6:

TABLE 5

| Formula | Appearance (color) after 3 months at 25° C. | Appearance (color) after 3 months at 40° C. | Appearance (color) after 6 months at 25° C. | Appearance (color) after 6 months at 40° C. |
|---|---|---|---|---|
| 10 | Pass (3) Light blue solution | Pass (3) Light blue solution | Pass (3) Light blue solution | Pass (3) Light blue solution with green shade |
| 1 | Pass (4) Light blue solution | Pass (4) Light blue solution | Pass (4) Light blue solution | Pass (3) Light blue solution with green shade |
| 7 | Pass (3) | Pass (3) Light blue solution | Pass (4) | Pass (4) |

TABLE 6

| Formula | Appearance (texture) after 3 months at 25° C. | Appearance (texture) after 3 months at 40° C. | Appearance (texture) after 6 months at 25° C. | Appearance (texture) after 6 months at 40° C. |
|---|---|---|---|---|
| 10 | Pass (3) Slightly turbid solution with traces of sediments | Pass (2) Slightly turbid solution with some sediments | Pass (2) Slightly turbid solution with slight sediments | Fail (1) Almost turbid solution with some sediments |
| 1 | Pass (4) Clear solution without sediments | Pass (4) Slightly turbid solution with some sediments | Pass (4) Clear solution without sediments | Pass (2) Slightly turbid solution with slight sediments |
| 7 | Pass (3) | Pass (3) Clear solution without sediments | Pass (4) Light blue clear | Pass (4) Light blue clear |

These results demonstrate that addition the composition of the present disclosure has acceptable turbidity and sediment formation.

As used throughout, ranges are used as shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight, in relation to the total weight of the composition. The amounts given are based on the active weight of the material.

Each of the patents, patent applications and other printed publications referred to herein are incorporated by reference in their entireties for all purposes.

While the present invention has been described with reference to embodiments, it will be understood by those skilled in the art that various modifications and variations may be made therein without departing from the scope of the present invention as defined by the appended claims.

What is claimed is:

1. An oral care mouth rinse composition comprising:
   at least one source of ionic tin;
   caprylyl glycol present in an amount of from 0.01% to 1% by weight of the composition;
   3-phenyl-1-propanol present in an amount of from 0.01% to 0.25% by weight of the composition; and
   methylpropanediol.

2. The oral care mouth rinse composition according to claim 1, wherein:
the caprylyl glycol is present in an amount of from 0.1% to 0.6% by weight of the composition; and
the 3-phenyl-1-propanol is present in an amount of from 0.02% to 0.15% by weight of the composition.

3. The oral care mouth rinse composition of claim 1 wherein the composition comprises at least one stannous ion source, at least one stannic ion source or a combination thereof.

4. The oral care mouth rinse composition of claim 1 wherein the composition comprises at least one stannous ion source.

5. The oral care mouth rinse composition of claim 1 wherein the at least one ionic tin source comprises stannous fluoride.

6. The oral care mouth rinse composition of claim 1 wherein the tin ions are present in an amount of from 0.01% to 0.10%; or from 0.02% to 0.08%; or from 0.03% to 0.06%; or from 0.035% to 0.045% by weight of the oral care mouth rinse composition.

7. The oral care mouth rinse composition of claim 1 further comprising a fluoride ion source which is not a tin salt.

8. The oral care mouth rinse composition of claim 1 further comprising an organic fluoride in an amount of from 0.01 to 0.4% by weight by weight of the composition.

9. The oral care mouth rinse composition of claim 8, comprising amine fluoride and stannous fluoride in an amount such that they together provide from about 0.01-0.04% fluoride ions by weight in the mouth rinse composition.

10. The oral care composition according to claim 9, wherein the stannous fluoride and the amine fluoride each provide fluoride ions in an amount of about 0.013% by weight of the composition.

11. The oral care mouth rinse composition according to claim 1, further comprising polyvinylpyrrolidone in an amount of from 0.1% to 3%; or from 0.1% to 4%; or from 0.15% to 2.5%, by weight of the composition.

12. The oral care mouth rinse composition according to claim 1, further comprising at least one $C_3$ to $C_7$ α-hydroxy acid, wherein, the at least one α-hydroxy acid is selected from malic acid, tartaric acid, α-hydroxy glutaric acid, gluconic acid, and a salt thereof.

13. The oral care mouth rinse composition according to claim 12 wherein, the at least one α-hydroxy acid or salt thereof is malic acid in an amount of from 0.01% to 0.8% by weight; or from 0.05% to 0.5% by weight; or from 0.08% to 0.3% by weight; or from 0.1% to 0.2% by weight of the composition.

14. The oral care mouth rinse composition according to claim 1, further comprising at least one surfactant.

15. The oral care mouth rinse composition according to claim 14, wherein the at least one surfactant comprises a PEG hydrogenated castor oil.

16. The oral care mouth rinse composition of claim 1 further comprising one or more humectants, sweeteners, flavorings, sensates, fragrances, dyes and odor neutralizing agents.

17. The oral care mouth rinse composition of claim 1 further comprising water in an amount of from 50% to 98% by weight of the oral care mouth rinse composition.

18. The oral care mouth rinse composition of claim 1, further comprising a dissolution agent selected from a surfactant, an amine, amine base, an organic fluoride, amine fluoride, propylene glycol, cocamidopropyl betaine, and mixtures thereof.

19. A method to:
(i) reduce or inhibit formation of dental caries,
(ii) reduce, repair or inhibit pre-carious lesions of the enamel,
(iii) reduce or inhibit demineralization and promote remineralization of the teeth,
(iv) reduce hypersensitivity of the teeth,
(v) reduce or inhibit gingivitis,
(vi) promote healing of sores or cuts in the oral cavity,
(vii) reduce levels of acid producing bacteria,
(viii) reduce or inhibit microbial biofilm formation in the oral cavity,
(ix) reduce or inhibit plaque formation in the oral cavity,
(x) promote systemic health, or
(xi) clean teeth and oral cavity,
comprising applying an effective amount of an oral care mouth rinse composition according to claim 1 to the oral cavity of a subject in need thereof.

* * * * *